(12) United States Patent
Mylonas et al.

(10) Patent No.: US 10,575,911 B2
(45) Date of Patent: Mar. 3, 2020

(54) SURGICAL DEVICE AND METHODS

(71) Applicant: IP2IPO Innovations Limited, Greater London (GB)

(72) Inventors: George Mylonas, Greater London (GB); Guang-Zhong Yang, Greater London (GB); Ara Darzi, Greater London (GB); Thomas Cundy, Greater London (GB)

(73) Assignee: IP2IPO Innovations Limited, Greater London (GB)

( * ) Notice: Subject to any disclaimer, the term of this patent is extended or adjusted under 35 U.S.C. 154(b) by 761 days.

(21) Appl. No.: 15/021,435

(22) PCT Filed: Sep. 10, 2014

(86) PCT No.: PCT/GB2014/052744
§ 371 (c)(1),
(2) Date: Mar. 11, 2016

(87) PCT Pub. No.: WO2015/036753
PCT Pub. Date: Mar. 19, 2015

(65) Prior Publication Data
US 2016/0220321 A1    Aug. 4, 2016

(30) Foreign Application Priority Data

Sep. 13, 2013  (GB) .................................... 1316333.2

(51) Int. Cl.
*A61B 34/00* (2016.01)
*A61B 18/14* (2006.01)
*A61B 18/00* (2006.01)

(52) U.S. Cl.
CPC .......... *A61B 34/71* (2016.02); *A61B 18/1487* (2013.01); *A61B 2018/00077* (2013.01); *A61B 2018/00577* (2013.01)

(58) Field of Classification Search
CPC ................................. A61B 34/71; A61B 34/00
See application file for complete search history.

(56) References Cited

U.S. PATENT DOCUMENTS

2011/0137129 A1* 6/2011 Heinrich .......... A61B 17/00234
                                                          600/206
2013/0190758 A1    7/2013 Smith et al.

FOREIGN PATENT DOCUMENTS

| EP | 2 329 789 | 6/2011 |
| WO | 2004/088467 | 10/2004 |
| WO | 2005/046500 | 5/2005 |

OTHER PUBLICATIONS

International Search Report and Written Opinion for International Patent Application No. PCT/GB2014/052744 dated Dec. 16, 2014.
International Preliminary Report on Patentability for International Patent Application No. PCT/GB2014/052744 dated Mar. 15, 2016.

* cited by examiner

*Primary Examiner* — Lynsey C Eiseman
(74) *Attorney, Agent, or Firm* — Wegman Hessler

(57) ABSTRACT

A surgical device (21) comprising a deployable peripheral structure (23) for insertion into a human or animal body, and one or more surgical tools (30) disposed at least partially within the deployable peripheral structure and having a plurality of tendons (24, 25, 26, 27) connected thereto operable to manipulate the or each surgical tool.

18 Claims, 5 Drawing Sheets

SURGICAL DEVICE AND METHODS

CROSS-REFERENCE TO RELATED APPLICATIONS

This application claims the priority filing benefit of International PCT Application PCT/GB2014/052744 filed Sep. 10, 2014 and published under PCT 21(2) in the English language, Great Britain Patent Application Serial No. GB 1316333.2 filed Sep. 13, 2013. Each of the above listed applications is incorporated herein by reference.

The present invention relates to surgical devices. In particular the invention relates to endoscopic or laparoscopic equipment for carrying out minimally invasive surgical procedures or biopsies and other test procedures.

Endoscopes are devices for looking inside the body, which typically include a light source and a means of transmitting an image from a region of interest inside the body to a physician. Many endoscopes also include surgical equipment or include internal channels through which surgical equipment can be inserted to the region of interest to perform surgery or biopsies etc. Laparoscopes are one such example. Henceforth, the term "scope" is used to cover all such devices for looking and/or operating in the human or animal body.

The initial first-generation era of minimally invasive surgery (MIS) was defined by a paradigm shift from traditional large open surgical incisions to multiple small 'keyhole' incisions. This transition provided many patient benefits, contributing to acceptance of MIS as standard surgical care in many settings. Today, there is growing momentum towards further minimising access trauma such that many procedures may be essentially 'scarless' when performed via single-incision laparoscopic surgery (SILS), natural orifice endoluminal surgery (NOES) and natural orifice transluminal endoscopic surgery (NOTES) techniques.

Known equipment for carrying out laparoscopic surgery includes traditional mechanically operated devices and various robotic or mechatronic prototype devices. These instruments are the current default platforms for SILS, NOES and NOTES. These techniques have achieved little progression beyond the experimental phase, despite nearly 10 years of committed effort at exploration and early assessment.

One example of a robotic surgery tool is the da Vinci Surgical System which is used by surgeons to replicate the same intra-corporeal surgical steps that would be undertaken using a conventional minimally invasive surgery approach. The putative benefits of robot-assistance are compelling, but are yet to translate to clear advantages affirmed by laudable evidence.

There are a number of prototype platforms for SILS, NOES and NOTES that are being developed worldwide by several academic groups. The majority of these prototypes attempt to exploit the benefits of robotic or mechatronic enhanced design to overcome challenges of the required single shaft bimanual actuating system. All current platforms remain in the pre-clinical phase with only a small number having reported feasibility in an in-vivo animal trial setting. Major limitations of emerging prototypes are almost universally shared. These pertain to adequate triangulation, force delivery, stability and control. Capability of any one prototype to break through to clinical translation and achieve meaningful impact is critically dependent on these requirements being met. The present invention seeks to address the issues of bimanual instrument triangulation and force-delivery.

An aim of the present invention is to provide a platform design that enables these new techniques to be more realizable in the short-term clinical setting. This approach promises a more immediate and accelerated route to clinical translation not only through low-cost and adaptive features, but also by directly addressing several major existing barriers in platform design.

The present invention provides a surgical device comprising a deployable peripheral structure for insertion into a human or animal body, and one or more surgical tools disposed at least partially within the deployable peripheral structure and having a plurality of tendons connected thereto operable to manipulate the or each surgical tool.

Advantageously, the device according to the invention allows surgery to be performed with only a single incision (internal or external) to the patient and only a single piece of equipment needs to be inserted into the patient.

By using tendons to control the surgical tool, the invention provides sufficient degrees of freedom in the movement of the tool to perform complicated tasks. The arrangement of tendons also allows strong forces to be applied to the tool, and allows well controlled, stable movements. A further advantage is that existing endoscopes can be modified to include the invention.

The invention also provides a method of performing surgery using a surgical device according to any of the preceding claims, comprising inserting the surgical device into the human or animal body and deploying the peripheral structure, then operating the arm using the tendons and using the surgical implement at the end of the arm to carry out a task.

There follows a detailed description of embodiments of the invention by way of example only and with reference to the accompanying drawings in which.

Figure 1:
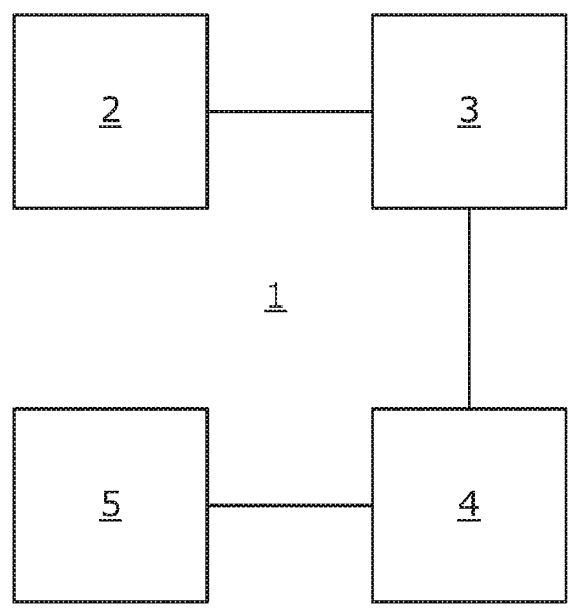
FIG. 1 is a schematic representation of a surgical system in accordance with an embodiment of the invention.

FIG. 1 shows a system 1 for carrying out surgical procedures comprising a manual input 2 connected to a control 3, which may comprise a PC or any other suitable processing device. The system further comprises a drive section 4 which includes several electric motors which are driven in accordance with control signals provided by the PC 3. Connected to the drive section is a surgical device 5 which includes an endoscopic shaft and a deployable peripheral structure (see FIG. 2) for insertion into a human or animal body. A series of tendons is connected from the drive section 4 to the surgical device 5 via the endoscopic shaft. Other cables such as electrical connections to working implements at the distal end of the device are entrained through the endoscopic shaft as well. The manual input can comprise a device which monitors the movement of a hand-held stick which is operated by the physician, and the motion of the stick is converted into corresponding motion at the output of the device. The manual input has as many degrees of freedom as the surgical tool that it controls. The system can include two manual inputs each controlling a surgical tool, whereby there is a correspondence between what the physician does with each hand and what occurs at the end of the surgical tools.

Figure 2:
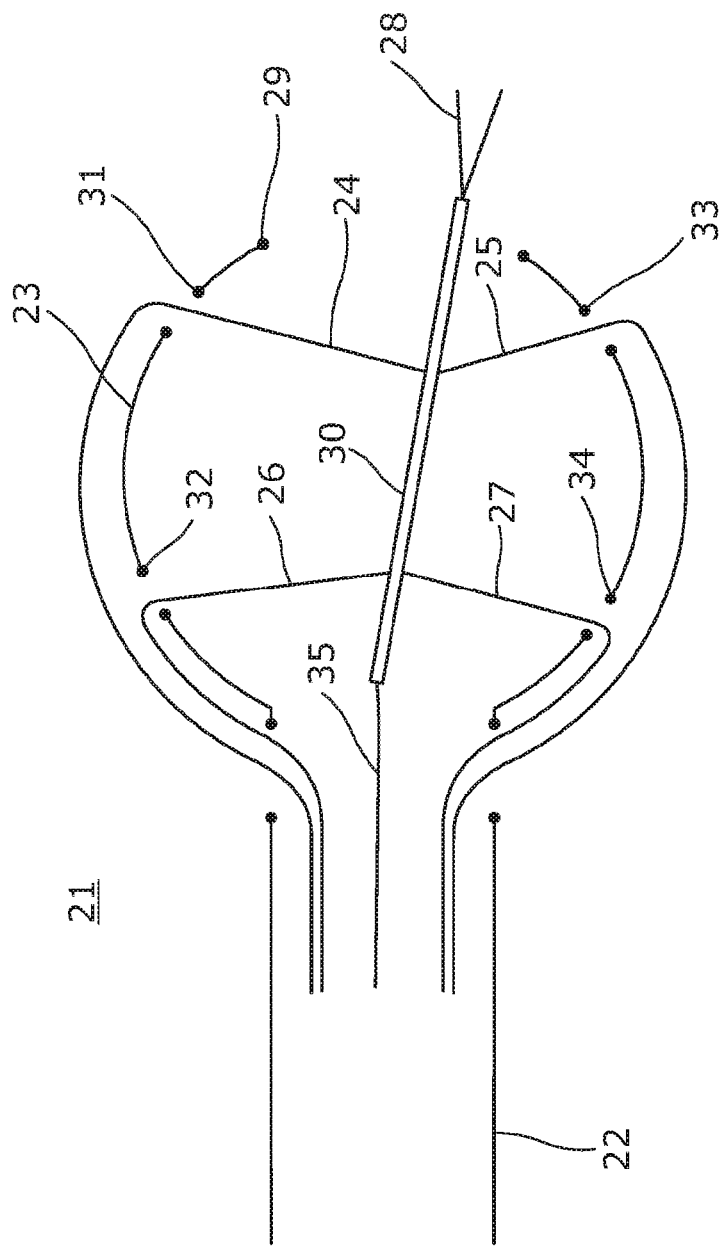
FIG. 2 is a schematic cross-section of a device embodying the invention.

FIG. 2 shows a cross section through a device 21 embodying the invention comprising an endoscopic shaft 22 at the end of which is disposed a deployable peripheral structure 23 comprising a bulb. The deployable peripheral structure 23 is shown in its deployed or inflated state and has a circular opening 29 at its front face through which a surgical tool 30 may protrude. The tendons 24 to 27 are directly connected to the surgical tool, which in this aspect is a bespoke working tool, whereas as described below it is also possible for the surgical tool to connect to an existing implement of a scope. One option in this regard is for the surgical tool to have a hollow tubular configuration which can be applied over an implement of existing scope equipment such that the device can be retrofitted. An implement, for example grasping or cutting means 28, is provided at the distal end of the arm 30. Other types of device can be located at the end of the surgical tool.

The tool is manipulated by means of a series of tendons, 24 to 27, only four of which are shown in FIG. 2. Each tendon extends from a connection point with the arm out of the deployable peripheral structure 23 via a guide 31 to 34 and along the outer side of the deployable peripheral structure 23 and into the endoscopic shaft 22 and back to the drive section. The guides 31 to 34 preferably comprise holes or eyelets in the surface of the deployable peripheral structure 23.

By virtue of extending along the curved surface of the deployable peripheral structure, the tendons can slide easily without snagging. A near correspondence between the force provided by the electric motors and the force provided at the ends of the tendons can be achieved. Each tendon has a corresponding motor which operates that tendon. A cable 35 extends from the arm 30 to the control or drive sections of the system and the cable allows control of the working implement situated at the end of the arm. The cable can be an electrical cable for providing electrical power to an end device such as a laser or electric motor for example, or it can be a mechanical link to allow operation of a mechanical device such as a forceps. In some embodiments, the surgical tool requires no cables, where it is solely controlled by the tendons.

Figure 3:
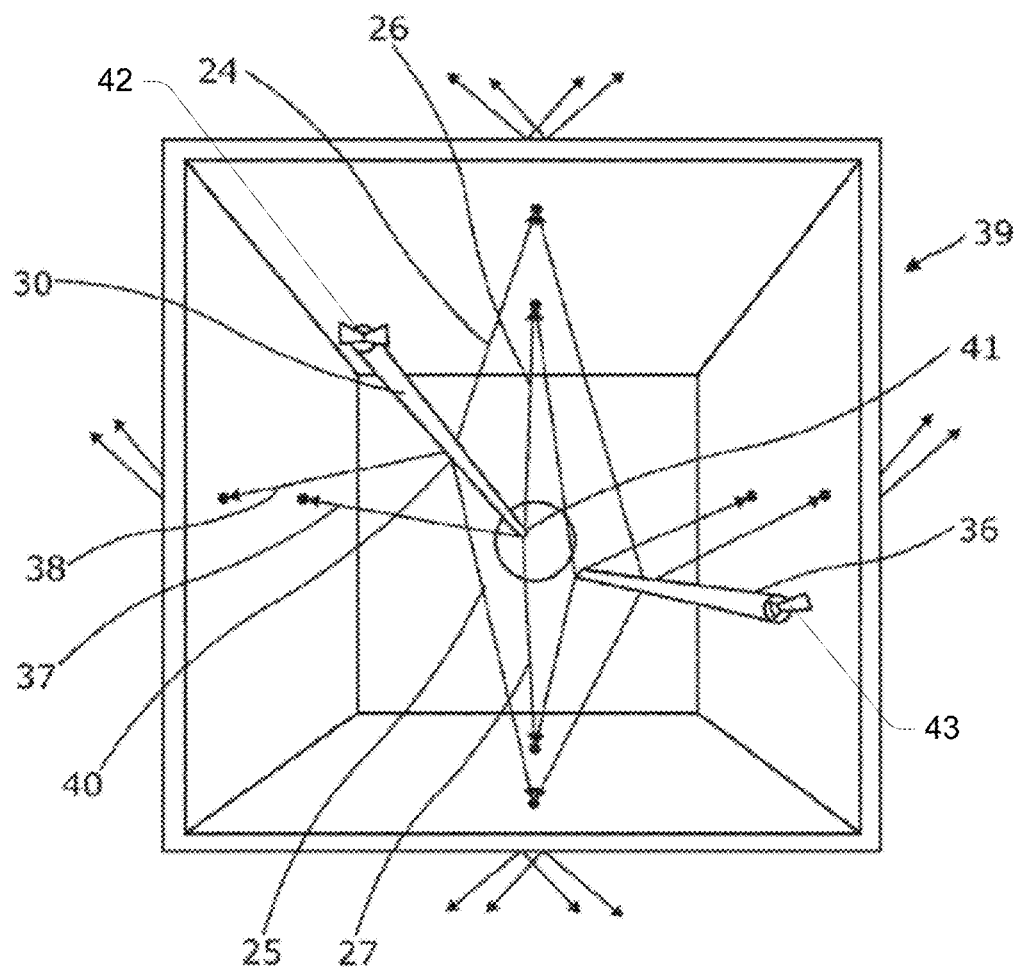
FIG. 3 is a schematic three-dimensional representation of a system which conceptually illustrates an embodiment the invention.

The arrangement of the tendons is shown in more detail in FIG. 3, in which the rigid deployable structure 39 has a cuboidal structure for the purposes of more clearly illustrating the function of the invention. It is generally preferred that the rigid deployable structure has a more spherical shape which is more ergonomically suited to placement in a human or animal body. In the example shown in FIG. 3 two surgical tools 30, 36 are provided. Each tool has a first set of three tendons 24, 25, 38 connected at a distal region of the tool, for example at connection point 40 and a second set of three tendons 26, 27, 37 which are connected at a proximal region, for example at connection point 41, of the tool 30. The tools have five degrees of freedom of movement, i.e. forward/backward, left/right, up/down, pitch and yaw. Another option, not shown in the drawings is to provide just one set of tendons at the distal end of the tool and to connect a cable or other link means at the proximal end of the tool so that the tool can be pulled into whatever desired position using the combination of the tendons and the link or cable.

In a further aspect of the device, it is possible to provide a $6^{th}$ degree of freedom, roll. One way in which this can be achieved is by an arrangement whereby the tendons are wrapped around the arm to some extent such that pulling the tendons tends to unravel them from the arm and causes the arm to rotate about its longitudinal axis.

In the arrangement shown in FIG. 3, the surgical tools 30, 36 comprise hollow tubes which receive an existing piece of scope equipment, which in the example shown is an implement comprising a pair of graspers 42, 43.

Figure 4:
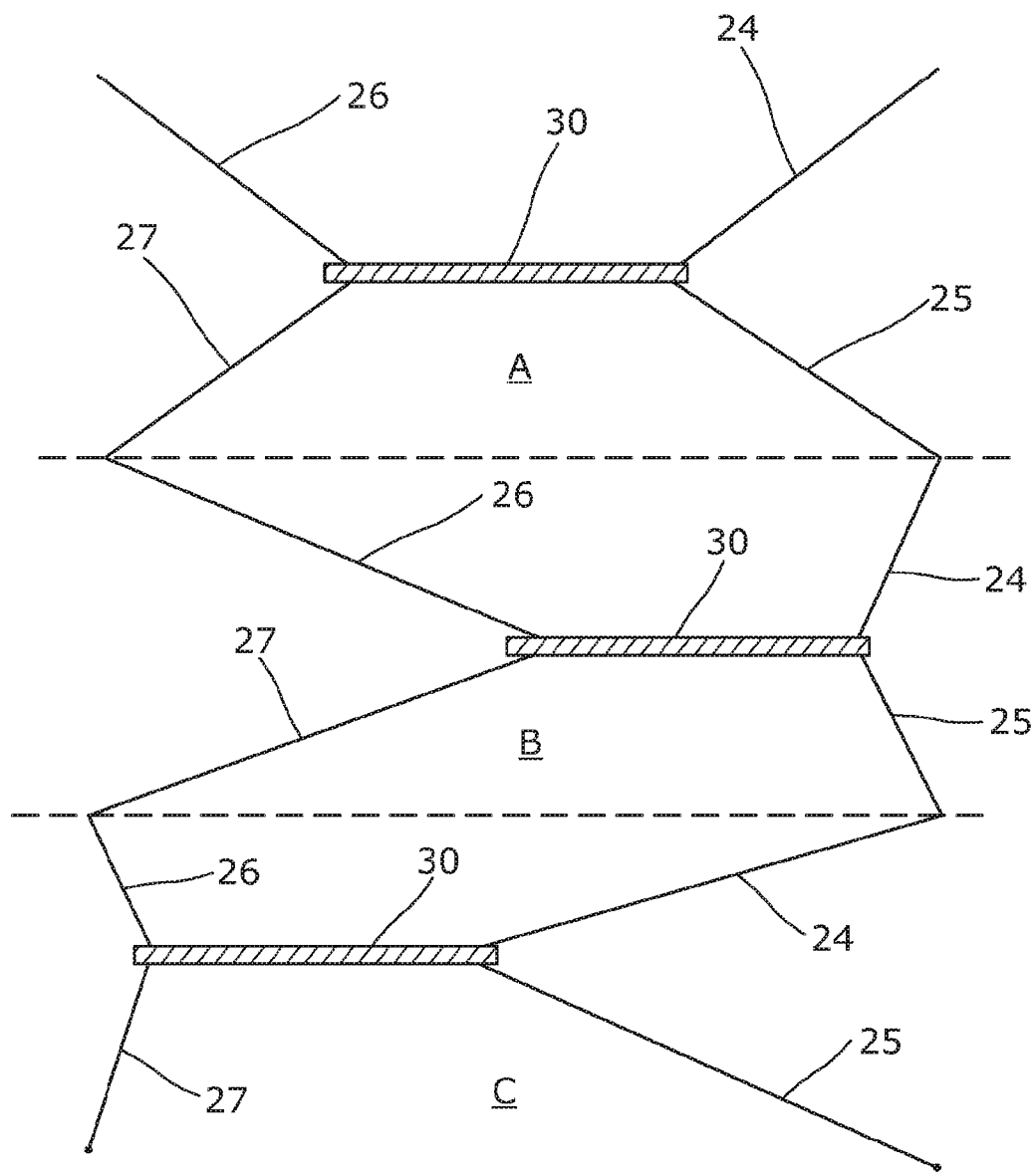
FIG. 4 is a schematic representation illustrating a further embodiment of the invention.

FIG. 4 shows schematically how the tendons effect movement of the arm. In the figure, section A shows the arm 30 in a neutral position, section B shows the arm 30 in a forward bias position and section C shows the arm in a rearward bias position. In order to move the arm from the position shown in section A to that shown in section B, tension is applied to the forward tendons 24, 25 and the arm 30 is pulled forwardly. To move the arm 30 to the rearward position shown in section C, tension is applied to the rear tendons 26, 27. By suitable manipulation of the tendons, any desired angle and position of the arm can be achieved. In order for the arrangement of tendons shown in FIG. 4 to apply an axial force to the tool, (i.e. along the longitudinal axis of the tool) the spacing between the guides or eyelets needs to be different to the spacing between the respective connection points on the tool. For example, as shown in FIG. 4, the guides are more spaced apart than the connection points on the tool, but alternatively, the guides could be more closely spaced than the connection points. This gives a non-parallel arrangement of tendons that allows axial force to be produced. The closer a tendon is aligned with a tool, the greater is the component of its force along the direction of the tool. In the case where the distance between the guides is the same as the distance between the respective connection points on the tool, it is still possible to move the tool in any position perpendicular to its axis and also to rotate the tool.

Figure 5:
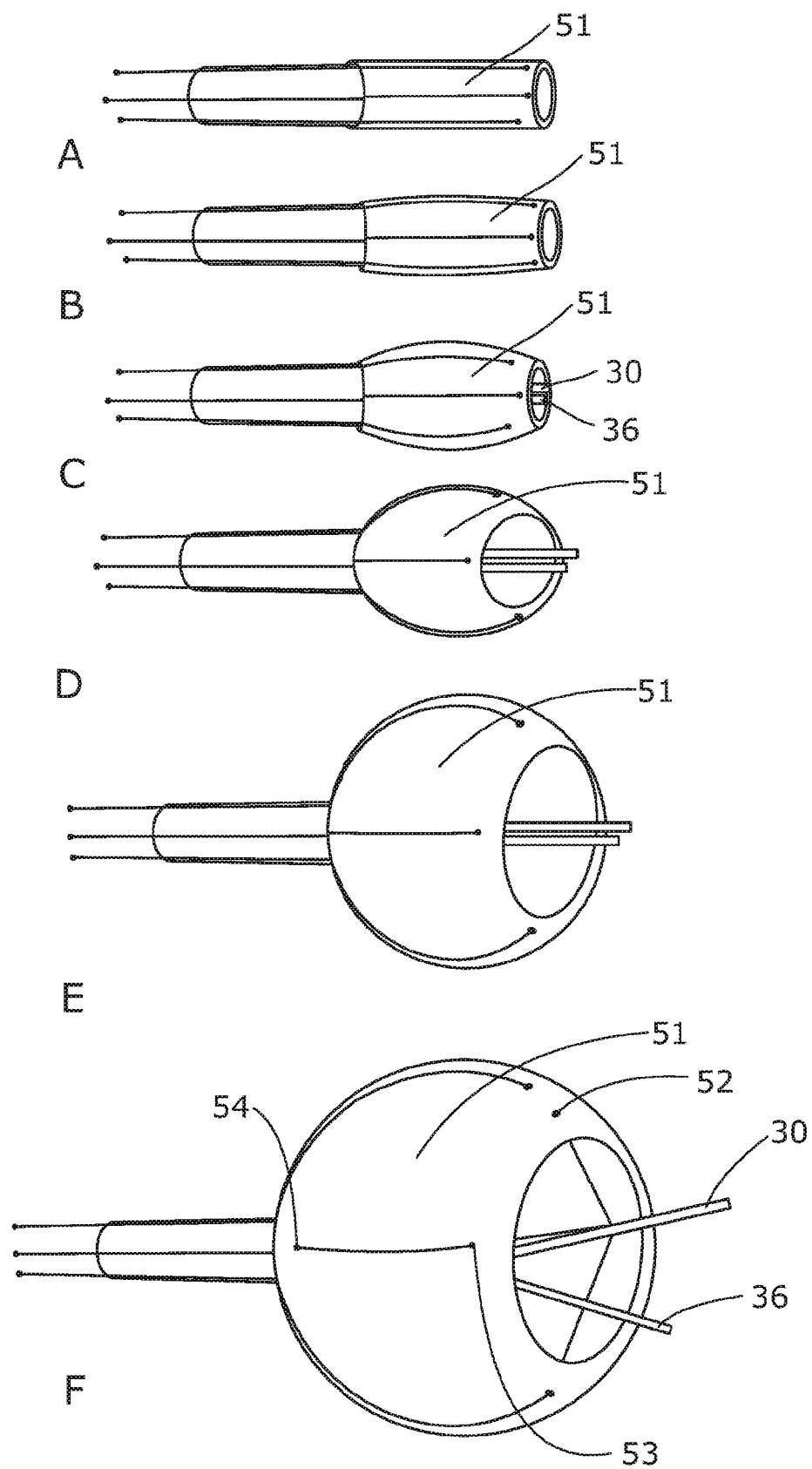
FIG. 5 is a sequence of drawings showing deployment of a peripheral structure in accordance with another embodiment of the invention.

FIG. 5 shows the stages of deployment of the deployable peripheral structure 51. In the embodiment shown, the deployable peripheral structure comprises an inflatable member which goes from a flat deflated configuration in section A to a fully inflated bulbous structure in section F. Eyelets 52, 53, 54 are provided in the deployable peripheral structure 51 for passage of the tendons. The deployable peripheral structure resembles an open-ended bulb with the arms protruding therefrom. The device is inserted into the body in the state shown in section A, i.e. uninflated. When the deployable peripheral structure has reached the desired region of interest within the body, it is begun to be inflated or otherwise deployed. The deployable structure can be a folding mechanism that is unfolded when in the desired position. Once the deployable peripheral structure is in position and fully deployed the physician can begin a surgical procedure using the tools.

As mentioned above, the structural elements of the device embodying the invention may be adapted and fitted to the distal end of a conventional laparoscope or flexible endoscope. This structure is low profile and un-obtrusive to the functionality of the main scope as it manoeuvres to the target operative anatomy. In a collapsed state ready for deployment, the bulb structure may be delivered and integrated at the distal scope end in several possible ways, such as a scope over-sheath, internal channel permissive 'probe', or pre-affixed distal scope cap attachment. Once appropriately located at the operative site, the structure is deployed in such a way that it expands radially outwards in a gradual and controlled manner to form an expanded semi-rigid scaffold that is covered with a soft sheet-like biocompatible material.

The size of the deployable peripheral structure or scaffold is scalable to suit procedural needs. Tendon fulcrum points positioned at lateral eyelets on the rigid bulb enable increased distal forces to be exerted by the working instruments and also a high degree of triangulation. From their most distal aspect, the tendons are networked through the body of the scaffold and then congregate at the bulb 'neck' where they are bundled through one of the available scope internal channels. A motorized driving unit provides computer-assisted actuation. Force feedback is also a feasible capability, whereby the user operating the device can sense what is happening inside the patient. In alignment with the low barrier approach to clinical translation that this design strives toward, interchangeable off-shelf flexible instruments and focused energy delivery devices may be delivered via existing internal channel(s) of the scope. Instruments may be immediately actuated by the above mechanism once docked within short 'clip-lock-and-play' rigid over-tubes that serve as attachment hubs for tendons. Additional tendons could also be used to control the position of other equipment within the scaffold, such as space floating cameras. The bulb is collapsible for extraction or extubation of the main instrument. The inner surface of the scaffold may serve valuable purpose by providing uniform multidirectional illumination based on reflection or diffusion of a native scope light source, or enhanced through a light-emitting material used as the internal wall of the scaffold. Due to the remote nature of the motor control and the materials in use, devices embodying the invention have the potential of MRI compatibility.

All of the tendons can remain under variable tension. Owing to their antagonistic nature and configuration, the tendons are able to exert high forces in 5 DoF while simultaneously ensuring control and stability of the instruments. With the insertion of a standard flexible grasper, an additional degree of freedom can be achieved, i.e. opening and closing of the jaws.

The deployable peripheral scaffold is subject to diverse requirements. The optimum solution ensures small initial packaging, a feasible deployment and removal strategy, compliance to the operative site and adequate rigidity of the fully deployed scaffold. It is possible to use structures such as Self-Deployable Tensegrity Structures, Origami and inflatable structures. The materials that can be used include Granular Jamming materials, Smart Materials, and Memory Materials. It is anticipated that bio-inspired design will play an important role at this stage. Site illumination can be provided either through reflection/diffusion of the scope's existing light source (similarly to an umbrella flash reflector) or though self illumination of the scaffold's internal wall (e.g., electroluminescent materials).

Integration with a standard endoscope can be achieved using a clip-on mechanism for example.

Enhanced screening programmes, improved imaging methods, and growing knowledge in biomarker identification are contributing to many tumours being diagnosed at an earlier stage. These circumstances generate mounting opportunity for organ preserving NOES. Endoscopic submucosal dissection (ESD) and mucosal resection (EMR) are gaining popularity in the gastroenterology community for treatment of low-grade neoplasms, however these remain almost prohibitively difficult due to inadequate platform technology. Low-grade tumours (i.e. T0 and T1) occurring in almost all hollow viscus structures may be considered candidates for an organ-preserving approach to curative resection. In this regard, 6 of the 20 cancers with the highest global incidence may be eligible, namely those involving the bowel, oesophagus, stomach, prostate, uterus, and bladder. The bulb structure of embodiments of the invention offers critical technical advantages beyond improved triangulation, force delivery, stability and control. Creation and maintenance of a submucosal space or tunnel is laborious and risky. Using the deployable bulb to mechanically expose and confidently maintain this working space presents a practical solution. Alternatively, the bulb may also be used to suction or invaginate tissue for resection as well as protecting it for safe specimen extraction. Finally, there are numerous imaging opportunities of the bulb design allowing the device to function well as an image acquisition and display device, ranging from multiple mobile camera positioning, improved illumination of the operative field and real time in-situ image-guided dissection using the bulb as a probe, for example a wide radial-array ultrasound probe.

A number of benign indications are also immediately apparent as potential roles for the embodiments of the invention in NOES. These include per-oral endoluminal myotomy (POEM), hysteroscopic myomectomy, and per-oral endoluminal bariatric surgery, for example.

In one alternative aspect, the device is operable by manual power alone, wherein the operating physician effects movement of the tendons using muscle power only and no electric motors are required. In this regard, it would be possible to provide a direct physical connection from the tendons at the working end of the device to the input means.

The invention claimed is:

1. A surgical device comprising a deployable peripheral structure for insertion into a human or animal body, a surgical tool disposed at least partially within the deployable peripheral structure, and a plurality of tendons connected to the surgical tool and operable to manipulate the surgical tool, wherein the surgical tool has a proximal region and a distal region, and the plurality of tendons comprise first and second sets of tendons, each set of tendons comprising three tendons, the first set of tendons being connected to the distal region of the surgical tool and the second set of tendons being connected to the proximal region of the surgical tool.

2. A surgical device according to claim 1 comprising an implement, wherein the surgical tool is arranged for releasable connection to the implement, whereby the tendons are operable to manipulate the implement.

3. A surgical device according to claim 2, wherein the surgical tool comprises a hollow tube for ensheathing the implement.

4. A surgical device according to claim 1, wherein the surgical tool comprises an implement and the tendons are directly connected to the implement.

5. A surgical device according to claim 1, wherein each tendon is arranged to pull in a different respective direction.

6. A surgical device according to claim 1, wherein the tendons are slidably anchored to the deployable peripheral structure, and the tendons are connected to the surgical tool via the deployable peripheral structure.

7. A surgical device according to claim 6, wherein the deployable peripheral structure comprises a plurality of guides and the tendons pass through guides.

8. A surgical device according to claim 7, wherein the guides comprise forward guides which are positioned forwardly on the deployable peripheral structure to allow forward biasing of the surgical tool and rearward guides which are positioned rearwardly on the deployable peripheral structure to allow rearward biasing of the surgical tool.

9. A surgical device according to claim 8, wherein the forward and rearward guides are separated by a first distance, and the tendons are connected to the surgical tool at respective connection points which are separated from each other by a second distance, wherein the first distance is different from the second distance.

10. A surgical device according to claim 9, wherein the first distance is greater than the second distance.

11. A surgical device according to claim 1, wherein at least one of the tendons comprises electrically conductive material and is usable to supply electrical power to the surgical tool.

12. A surgical device according to claim 1, wherein the deployable peripheral structure is collapsible to a collapsed position and deployable from the collapsed position to a deployed position.

13. A surgical device according to claim 1, wherein the deployable peripheral structure has a generally spheroidal shape when deployed.

14. A surgical device according to claim 13, wherein the deployable peripheral structure has an open-faced bulb shape when deployed, the surgical tools being protrudable from the open face of the bulb.

15. A surgical device according to claim 1, wherein the surgical tool has a plurality of degrees of freedom, and the device further comprises a control input having the same number of degrees of freedom as the surgical tool.

16. A surgical system comprising a surgical device comprising a deployable peripheral structure for insertion into a human or animal body, a surgical tool disposed at least partially within the deployable peripheral structure, a plurality of tendons connected to the deployable structure and operable to manipulate the surgical tool, wherein the surgical tool has a proximal region and a distal region, and the plurality of tendons comprise first and second sets of tendons, each set of tendons comprising three tendons, the first set of tendons being connected to the distal region of the surgical tool and the second set of tendons being connected to the proximal region of the surgical tool; and
   an implement arranged to be connected to the surgical tool.

17. A method of performing surgery using a surgical device according to claim 1, comprising inserting the surgical device into the human or animal body and deploying the peripheral structure, then operating the surgical tool via the tendons and using the surgical implement to carry out a surgical task.

18. A method according to claim 17, wherein the surgery carried out comprises at least one of a transluminal procedure, an endoluminal procedure and an intracavity (i.e. transperitoneal) procedure, wherein the procedure is at least one of ablative and reconstructive in nature.

* * * * *